United States Patent [19]

Koekemoer

[11] 3,993,498

[45] Nov. 23, 1976

[54] GRANULAR CARRIER MATERIAL

[75] Inventor: Gerald John Koekemoer, Verwoerdburg, South Africa

[73] Assignee: Cullinan Holdings Limited, South Africa

[22] Filed: Mar. 31, 1975

[21] Appl. No.: 563,883

[30] Foreign Application Priority Data

Apr. 8, 1974  South Africa.................... 74/2247

[52] U.S. Cl.................................. 106/288 B; 241/3; 241/17; 241/30
[51] Int. Cl.².................. C04B 31/40; B02C 19/12
[58] Field of Search................. 241/3, 4, 15, 17, 21, 241/23, 25, 30; 252/449, 455 R, 378 P; 106/72, 288 B, DIG. 2, DIG. 4

[56] References Cited
UNITED STATES PATENTS

| | | |
|---|---|---|
| 2,363,876 | 11/1944 | La Lande, Jr. .................... 241/3 |
| 2,728,733 | 12/1955 | Hashimoto .......................... 252/449 |
| 2,935,267 | 5/1960 | Maxey ................................. 241/17 |
| 2,956,016 | 10/1960 | Leppla .............................. 106/288 B |
| 2,967,154 | 1/1961 | Beerman .............................. 252/449 |
| 3,041,238 | 6/1962 | Allegrini ............................ 241/23 |

Primary Examiner—Granville Y. Custer, Jr.
Attorney, Agent, or Firm—Ladas, Parry, Von Gehr, Goldsmith & Deschamps

[57] ABSTRACT

A granular carrier material and process for producing same adapted for use with pesticides. A cake is formed of an intimate mixture of 97–80% by weight attapulgite and 3–20% by weight perlite, the attapulgite and perlite being capable of passing through a 150 ASTM mesh screen. The cake is then heated to a temperature of 450°–780° C. and is broken to form a granular solid.

27 Claims, No Drawings

GRANULAR CARRIER MATERIAL

BACKGROUND OF THE INVENTION

1. Field of the Invention

This invention relates to the production of a granular carrier material for pesticides from attapulgite, and to a carrier material produced according to the method.

In this specification "attapulgite" means both pure or high grade attapulgite and impure or low grade attapulgite. "Impure attapulgite" includes minerals which comprise a major proportion of attapulgite, together with substances, e.g. magnesium and calcium carbonates, which can be regarded as impurities, because they reduce the absorbency of the impure attapulgite, when compared with pure attapulgite. This impure or low grade attaplugite is regarded commercially and industrially as unsuitable for use as a carrier material, as explained hereunder, for solid state pesticides, when compared with high grade attapulgite.

One of the useful properties of attapulgite is that when dry, it absorbes water to a lesser or greater extent, depending on its purity. This renders it useful when it is desired to absorb liquids. For example, attapulgite may be used to form cat litter, or it may be used as a carrier material for pesticides in agriculture, the latter being an important commercial application in which use is made of the absorbency (sorptivity) of attapulgite with respect to liquids.

When attapulgite is dried by heating up temperatures of say, between about 150° and 200° C, it undergoes no structural change. Thus, when water is added to the dried attapulgite, it reverts to its original state.

On the other hand, when attapulgite is heated or fired to temperatures between about 250° and about 800° C, it loses further water but at the same time undergoes an irreversible chemical change. The water which is driven off between about 250° and about 800° C comprises chemically bound water or the constituents thereof, which are present in the original attapulgite in the form of, principally, lattice water, water of crystallization and hydroxyl groups. Upon heating to between about 250° and about 800° C, the attapulgite undergoes an irreversible change, although its structure, apart from the loss of the chemically bound water, remains substantially unchanged. Whereas attapulgite which has not been fired forms a more or less plastic mixture with water and forms a suspension in water, the fired product does not do so and separates rapidly and easily from water in which it is dispersed. Furthermore, the absorbency with respect to liquids of the fired product, particularly when fired to temperatures in the range between about 500° and 800° C, is superior to that of the original attapulgite.

Finally, when attapulgite is heated to temperatures above about about 800° C, it undergoes a irreversible chemical and structural change, which is complete at temperatures above 1000° C, in which its physical and chemical properties are altered, the product having an absorbency with respect to liquids which is less than that of the original attapulgite.

In agriculture, solid state pesticides are extensively used for pest control. Solid state pesticides comprise liquid toxicants, e.g. insecticides, herbicides, miticides, fungicides and rodenticides, and a solid granular diluent or carrier material, the toxicant being absorbed into the carrier material.

Generally, the toxicant makes up between 1 and 40% by weight of the pesticide, the carrier material making up the balance. A suitable carrier material is preferably chemically inert with respect to most commonly used toxicants and has the following desirable properties:

Granularity — The carrier material should be capable of forming small granular particles, so that the carrier material in bulk is a free flowing granular solid.

Stability in use — The carrier material should be of sufficient density for particles thereof to remain in position on soil or foliage to which they have been applied in windy conditions; and should be water-resistant in that they resist deterioration and do not physically decompose or collapse into a runny sludge in rainy conditions. The carrier material should also be substantially unaffected by changes in temperature and humidity encountered in transportation, storage and use.

Absorbency (Sorptivity) — The carrier material should be capable of absorbing the prescribed amounts of toxicants for each intended application; and it should at the same time remain a free flowing and relatively dry feeling granular solid when the toxicant is absorbed therein. Absorption should take place rapidly and easily on contact of the carrier material with most toxicants, and the carrier material should be easily wettable by toxicants.

Compatibility — The carrier material should be both physically and chemically compatible with most toxicants, i.e. the carrier material should not react chemically with the toxicants or deteriorate physically when in contact with them, and it should not cause deterioration of the toxicants.

Retentivity — The carrier material should release the pesticide to the atmosphere at a controlled, uniform and preferably slow rate, thereby to achieve vaporization of the toxicant at a controlled release rate over a predetermined period of time.

Resistance to Attrition — The carrier material should resist attrition so that dust generation is kept within allowable limits during normal handling in transport, storage, application and use. Dust can adversely affect the bulk handling of the carrier material and can be lost in application and use in windy conditions.

In practice the carrier materials is frequently shipped in bulk to compounders of pesticides, and a compounder may wish to make several different types of pesticides, depending on the toxicant used, from the same carrier material. A good carrier material should thus be capable of use with most toxicants and the applicant has found that, to be a commercially practical product, the carrier material should be capable of absorbing a test liquid (defined hereunder) so that the test liquid makes up about 30 to 40% of the pesticide product.

In the past, high grade (with respect to absorbency) attapulgite has been extensively used as a carrier material. Attapulgite is a clay which is found in deposits in relatively few localities, principally in Georgia, U.S.A. of sufficient quality to be used as a carrier material. There are other large deposits, in the U.S.A. and elsewhere, of low grade attapulgite, which are not suitable for use as a carrier material, having an absorbency which is too low to meet the more exacting applications. The invention thus finds particular application in increasing the absorbency, after firing, of low grade attapulgite, to levels acceptable for use as a carrier material.

2. Description of the Prior Art

In the past, it has been known to increase the absorbency of attapulgite for use as a granular carrier material. The prior art discloses the heating or calcining of attapulgite to temperatures between about 250° and about 800° C, the attapulgite losing water and undergoing an irreversible chemical change. A product is obtained which is substantially superior to the unfired attapulgite, as an absorbent of pesticides, for use as a granular carrier material. The absorbency of the fired product with respect to liquids is increased, as is the resistance to attrition thereof; and it forms a suspension less readily in water than the original attapulgite, and separates more easily from water in which it is dispersed.

SUMMARY OF THE INVENTION

According to the invention a process for producing a granular carrier material for pesticides from attapulgite includes the steps of:

a. wet mixing perlite and attapulgite together in an aqueous medium to form a cake which comprises an intimate mixture of between 97 and 80% by weight of attapulgite in finely divided form and between 3 and 20% by weight of heat expanded perlite in finely divided form, the attapulgite and perlite being of a particle size capable of passing through a 150 mesh ASTM screen;

b. heating the cake to a temperature of between 450° and 780° C; and c. breaking up the cake to form a granular solid.

By "heat expanded perlite" is meant perlite which has been heated to a temperature, between 1000° and 1500° C, and at which it undergoes a substantial increase in volume with a corresponding decrease in bulk density. In this specification, all references to "perlite" mean heat expanded perlite.

The temperature to which the cake is heated may be balanced against the relative proportions of attapulgite and perlite in the mixture to achieve a desired absorbency with respect to liquids in the product. The temperature to which the cake is heated may be balanced against the relative proportions of attapulgite and perlite to obtain a carrier material capable of absorbing a liquid comprising 77% by weight of benzyl chloride (alpha chloro toluene) and 23% by weight of petroleum benzine to form a free-flowing granular product comprising at least 30% by weight of the liquid.

The mixture may be formed to have between 92 and 85% by weight of attapulgite, and between 8 and 15% by weight of perlite.

Heating the cake may be to a temperature of between 500° and 700° C, preferably to a temperature between 500° and 600° C.

The process may include the step of, after heating the mixture, maintaining the mixture at the temperature to which it is heated for a soaking period of up to three hours. The soaking period may be between one and two hours.

Forming the cake may include wet mixing the components of the mixture together in an aqueous medium, followed be drying to form the cake. The wet mixing may comprise dispersing the components in the aqueous medium, the mixture being separated from the aqueous medium prior to drying. Separating the mixture from the aqueous medium may be by causing it to settle from the aqueous medium; and the settling may include flocculating the components by means of an organic flocculant.

The wet mixing includes adding phosphoric acid to the mixture so that the phosphoric acid forms 0.2 to 0.5% by weight of the total weight of the mixture on a dry basis, so as to increase the resistance to attrition of the granular material formed. In other words, during the wet mixing the phosphoric acid is added in an amount equal to between 0.2 and 0.5% by weight of the total dry weight of the solids in the mixture.

Forming the mixture may be by a mixing step in which comminuting of the components of the mixture takes place. The particle size of the components in the cake may be such that the greater proportion by weight of the particles will pass through a 200 ASTM mesh screen but will be retained by a 600 ASTM mesh screen. Preferably said particle size is such that the greater proportion by weight of the particles will pass through a 300 ASTM mesh screen but will be retained by a 400 ASTM mesh screen.

The breaking step may comprise grinding, the process including the step, after grinding the cake, of classifying the particles formed according to size so that at least 80% by weight of the carrier material will pass through a 20 mesh ASTM screen but will be retained by a 60 mesh ASTM screen. The classifying may be by screening, being such as to classify the particles into predetermined fractions, according to size, the screening being followed by the step of recombining the fractions in predetermined proportions to obtain a granular product of desired particle size distribution.

A proportion of the particles may be recycled through the grinding step for additional grinding. A further proportion of the particles may be recycled through the mixing step to form part of the cake.

The invention extends also to a carrier material for pesticides, produced according to the method.

The applicant has found that, for practical purposes, attapulgite suitable after firing for use as a carrier material should have an absorbency or liquid holding capacity (LHC) with respect to a test liquid comprising a mixture of 77% by weight of benzyl chloride and 23% by weight of petroleum benzine of 31% where:

$$\% \text{ LHC} = \frac{\text{weight of test liquid} \times 100}{\text{weight of test liquid} + \text{weight of carrier material}}$$

In other words a carrier material with LHC of 31% according to the above formula with respect to said mixture of benzyl chloride and petroleum benzine is suitable for use in bulk as a carrier material for solid state pesticides.

The test method used comprises placing 10 g of carrier material in a 6 oz. stoppered glass bottle. 5 ml increments of test liquid were added to the carrier material by means of a burette and after each addition the bottle was shaken vigorously by hand either until no granules clung to the sides of the bottle (in which case a further addition of test liquid was made) or for 5 minutes. When sufficient liquid had been added to ensure that granules still clung to the sides of the bottle after shaking for 5 minutes, further carrier material was added in 1 g. increments. The bottle was shaken after each 1 g. addition of carrier material for 5 minutes. The test was stopped when sufficient carrier material had been added to prevent adherence of granules to the sides of the bottle. The LHC was then calculated according to the above formula, using the total weight of test liquid and the total weight of carrier material in the bottle.

Resistance to attrition and apparent density (mentioned hereunder) were tested respectively by tumbling the carrier material with metal balls in a laboratory tumbler to determine the amount of fines produced, and by placing a predetermined weight of carrier material in a measuring cylinder and tapping the cylinder in a controlled fashion a number of times before measuring the volume occupied in the cylinder by the carrier material.

DETAILED DESCRIPTION OF THE INVENTION

The invention will now be described, by way of example, with reference to the following non-limiting examples, which refer to investigations carried out by the applicant relating to changes in absorbency of attapulgite, brought about by heat treatment, processing methods, and additions to the attapulgite.

Example 1

Inherent Absorbencies of Low Grade Attapulgite

Tests were conducted to determine the inherent absorbency of attapulgite, after it had been subjected to certain process steps.

The attapulgite tested was a representative low grade attapulgite clay from the Springbok Flats area of the Northern Transvaal and which included a substantial proportion of carbonate impurities.

The tests were carried out with a view to determining the effects on absorbency brought about by variations in temperatures to which the attapulgite was heated, and brought about by variations in the particle sizes of the attapulgite.

Samples of attapulgite were dried at 120° C until substantially constant weight. The samples were then crushed, milled and screened into various fractions according to particle size. In this example and the following examples the screen sizes, i.e. the sizes of the openings in the screens, are expressed in microns. Each fraction of screened clay is indicated by two numbers, the first preceded by a minus sign, and the second preceded by a plus sign. This means that the particles of the fraction are smaller than, and will pass through, the openings of a screen in which the openings have a size equal to the first number, but will be retained on a screen on which the openings are of the size indicated by the second number. Thus, for example, a fraction of screened particles having the designation −850, +600 means that all the particles of the fraction will pass through a screen having openings of 850 micron size, but will all be retained by a screen having openings of 600 micron size.

The various samples of attapulgite tested were screened to give the following fractions according to particle size:

| (a) −850, + 600 | (c) −425, + 300 |
|---|---|
| (b) −600, + 425 | (d) −80 |

Each of the four fractions obtained for the attapulgite was split into three equal portions designated portions A, B, and C.

Portion A was redried at 120° C for 2 hours;

Portion B was fired at 500° C and soaked at this temperature for 2 hours; and

Portion C was fired at 750° C and soaked at this temperature for 2 hours.

Absorbency (sorption) tests were then conducted, according to the test method described above with the test liquid described above, and also with kerosene as a test liquid. The results of these tests are set out as follows in Table 1.

TABLE 1

Detailed liquid holding capacity values

| Treatment | Particle size fraction | Liquid holding capacity Attapulgite | |
|---|---|---|---|
| | | Kerosene | Test Liquid |
| Portion A | −850, + 600 | 17.35 | 21.19 |
| Dried at | −600, + 425 | 17.35 | 21.19 |
| 120° C for | −425, + 300 | 18.02 | — |
| 2 hours | −80 | 31.02 | — |
| Portion B | −850, + 600 | 18.02 | 21.94 |
| Fired at | −600, + 425 | 19.35 | 24.11 |
| 500° C for | −425, + 300 | 20.62 | 25.49 |
| 2 hours | −80 | 31.96 | — |
| Portion C | −850, + 600 | 23.07 | 26.82 |
| Fired at | −600, + 425 | 23.07 | 27.47 |
| 750° C for | −425, + 300 | 24.80 | 29.96 |
| 2 hours | −80 | 35.88 | — |

TABLE 11

The test results of Table 1, averaged over a particle size distribution of −850, +300 are set out in Table 11.

| Treatment | Liquid holding capacity Attapulgite | |
|---|---|---|
| | Kerosene | Test liquid |
| Portion A Dried at 120° C for 2 hours | 17.6 | 21.4 |
| Portion B Fired at 500° C for 2 hours | 19.3 | 23.8 |
| Portion C Fired at 750° C for 2 hours | 23.7 | 28.1 |

In the preceding two Tables, as in the succeeding Examples, liquid holding capacity is expressed as a percentage. For practical purposes for use as a solid state diluent or carrier material a minimum liquid holding capacity of at least 30 and preferably above 31 with respect to the test liquid is required for a carrier having a particle size distribution made up of equal portions of a −600, + 425 fraction and a −425, + 300 fraction.

CONCLUSIONS

The liquid holding capacity of the attapulgite tested increased with increases in firing temperature; Higher liquid holding capacities were attained with decreases in particle size.

In each case the liquid holding capacity with respect to Kerosene was less than that for the test liquid. The test liquid is the standard against which the liquid holding capacity is measured, and the tests with Kerosene serve to confirm that liquid holding capacity increases with firing temperature, and increases together with decrease in particle size.

EXAMPLE 2

Absorbency of Constructed Granules With No Additions

The following tests were conducted to determine the absorbencies of attapulgite, which had been ground and milled, then formed into a cake, and then reground, milled and screened. The tests were carried out on the same attapulgite according to the following test method:

Samples of attapulgite were dried at 120° C to constant weight, crushed, milled and screened to give;
a. A powder having a particle or grain size of −200; and
b. A powder having a particle size of −45.

From each of the powders granules, arbitrarily designated A-type granules, B-type granules and C-type granules, were constructed as follows:

A-TYPE GRANULES

A portion of the −200 powder was treated with excess water until all the material was in suspension. Suspended particles were allowed to settle and excess water was decanted. The residue was dried at 120° C until a cake was formed. The cake was crushed, milled and screened to produce granules designated A/C-type, wherein A designates the arbitrary granule type and C designates the use of −200 powder that was treated, of the following fractions:
i. −850, +600
ii. −600, +425
iii. −425, +300

The same procedure was followed with the −45 powder to produce granules, designated A/F-type, wherein F designates −45 powder being used therein.

B-TYPE GRANULES

The procedure for A-type granules was repeated except that settling of the suspended particles was accelerated by use of an organic flocculant presently available from Protea Holdings Limited, Pretoria, Transvaal Province, Republic of South Africa, under the trade designation SUPERFLOC. Granules designated B/C-type were produced from a portion of the −200 powder and granules designated B/F-type were produced from a portion of the −45 powder.

C-TYPE GRANULES

The procedure for A-type granules was repeated, except that instead of forming a suspension of the particles of the powder followed by settling and drying to form the cake, the cake was formed by mixing sufficient water with the powder to form a plastic product, after which the drying took place. Granules designated C/C-type were produced from the −200 powder, and granules designated C/F-type were produced from the −45 powder.

The granule types A/C, A/F, B/C, B/F, C/C and C/F were then each divided into three equal portions, of which:
One portion was dried at 120° C for 2 hours;
One portion was fired to 500° C and soaked at this temperature for 2 hours; and
One portion was fired to 750° C and soaked at this temperature for 2 hours.

Absorbency tests were then carried out to establish the liquid holding capacity of the various constructed particles. The tests were carried out using Kerosene as absorbate. The results are set out in Tables III to VII hereunder.

TABLE III

Liquid holding capacities for granules constructed from attapulgite

| Particle size fraction | Type granule | Liquid holding capacity | | |
|---|---|---|---|---|
| | | Dried at 120° C | Fired 500° C | Fired 750° C |
| −850, +600 | A/C | 20.2 | 20.8 | 21.4 |
| −600, +425 | A/C | 18.9 | 19.5 | 21.4 |
| −425, +300 | A/C | 18.3 | 19.5 | 20.8 |
| −850, +600 | A/F | 16.9 | 16.9 | 18.3 |
| −600, +425 | A/F | 16.9 | 18.3 | 18.9 |
| −425, +300 | A/F | 17.6 | 18.3 | 18.9 |
| −850, +600 | B/C | 18.9 | 20.2 | 21.4 |
| −600, +425 | B/C | 19.5 | 20.2 | 21.4 |
| −425, +300 | B/C | 17.6 | 19.5 | 20.8 |
| −850, +600 | B/F | 16.3 | 17.6 | 18.9 |
| −600, +425 | B/F | 16.9 | 17.6 | 19.5 |
| −425, +300 | B/F | 17.6 | 18.9 | 19.5 |
| −850, +600 | C/C | 18.3 | 17.6 | 20.2 |
| −600, +425 | C/C | 19.5 | 19.5 | 20.2 |
| −425, +300 | C/C | 18.3 | 19.5 | 20.8 |
| −850, +600 | C/F | 16.9 | 19.5 | 19.5 |
| −600, +425 | C/F | 17.6 | 18.3 | 19.5 |
| −425, +300 | C/F | 17.6 | 18.3 | 19.5 |

The liquid holding capacities, averaged over the particle size distribution of −850, +300 are set out in Table IV below.

TABLE IV

Liquid holding capacities for fraction − 850, + 300

| Treatment | Type granule | Liquid holding capacity Attapulgite |
|---|---|---|
| Dried at 120° C 2 hours | A/C | 19.1 |
| | A/F | 17.1 |
| | B/C | 18.7 |
| | B/F | 16.9 |
| | C/C | 18.7 |
| | C/F | 17.4 |
| Fired at 500° C 2 hours | A/C | 19.9 |
| | A/F | 17.8 |
| | B/C | 19.9 |
| | B/F | 18.0 |
| | C/C | 18.9 |
| | C/F | 18.7 |
| Fired at 750° C 2 hours | A/C | 21.2 |
| | A/F | 18.7 |
| | B/C | 21.2 |
| | B/F | 19.3 |
| | C/C | 20.4 |
| | C/F | 19.5 |

CONCLUSIONS

Effect of Starting Powder Size

Granules constructed from −200 powder had a greater liquid holding capacity than those produced from −45 powder.

Comparison of Constructed Granules to Natural Granules With Respect to Liquid Holding Capacity Natural granules had a higher liquid holding capacity than all the types of constructed granules tested. The superiority with respect to liquid holding capacity is most apparent at elevated temperatures.

Heat Activation Effects

In all cases the liquid holding capacity increased with increases in firing temperature.

Portions 2 in each case were fired at 500° C and soaked for 2 hours; and
Portions 3 in each case were fired at 750° C and soaked for 2 hours.

Absorbency tests were then conducted in the manner described above to establish the liquid holding capacity using both Kerosene and test liquid as absorbates, as shown in Table V below.

TABLE V

Liquid holding capacities for constructed granules having an overall particle size distribution of −850, + 300

| Perlite Addition | 0% | | 5% | | 10% | | 15% | | 20% | |
| --- | --- | --- | --- | --- | --- | --- | --- | --- | --- | --- |
| Heat Treatment | Kerosene | Test liquid | Kerosene | Test liquid | Kerosene | Test liquid | Kerosene | Test liquid | Kerosene | Test liquid |
| Drying at 120° C for 2 hours | 17.6 | 24.3 | 22.6 | 30.4 | 24.9 | 32.8 | 26.5 | 34.4 | 29.5 | 36.5 |
| Fired at 500° C and soaked for 2 hours | 20.8 | 24.5 | 25.4 | 32.8 | 27.0 | 34.9 | 29.0 | 35.5 | 30.9 | 37.5 |
| Fired at 750° C and soaked for 2 hours | 23.8 | 30.4 | 27.5 | 33.3 | 29.5 | 36.6 | 32.3 | 40.7 | 33.2 | 42.9 |

Grain Size Effects

There appeared to be no trend which could be ascertained, as regards grain or particle sizes of the constructed granules with respect to liquid holding capacity.

EXAMPLE 3

Effect on the Absorbency of Attapulgite in the Form of Constructed Particles With Additions of Perlite A representative Springbok Flats attapulgite was tested with respect to liquid holding capacity, when in the form of constructed granules having various additions of perlite.

The attapulgite was dried at 120° C, crushed, milled and screened to a powder having a grain size of −200. The various powders were then split each into five equal portions designated A, B, C, D, and E. Finely divided perlite, of a particle size small enough to pass through a 300 ASTM mesh screen was added to the various portions as follows:

Portion A — no perlite
Portion B — 5% perlite added by weight
Portion C — 10% perlite added by weight
Portion D — 15% perlite added by weight
Portion E — 20% perlite added by weight After the addition of perlite dry mixing took place, and each portion was treated with excess water until all the material was in suspension. "SUPERFLOC" was used to produce flocculation and accelerate settling, and excess water was then decanted. The residue was then dried, crushed, milled and screened to give the following fractions:
−850, + 600
−600, +425
−425, + 300

Equal amounts by weight of each fraction were then combined to form portions A/0, B/5, C/10, D/15 and E/20 each having an overall particle size distribution of −850, +300. Each of these portions was then split to a further three equal portions designated 1, 2 and 3 (i.e $A_1/O$, $A_2/O$, $A_3/O$ etc.)

Portions 1 in each case were dried at 120° C for 2 hours;

CONCLUSIONS

From Table V it is clear that an increase in liquid holding capacity results when perlite is mixed into attapulgite in the increasing proportions indicated. From this Table it is also clear that liquid holding capacity increases, regardless of the percentage of perlite added, for an increase in the firing temperature. It is also apparent that when between 5 and 20% perlite is added, and when firing is to a temperature between 500° and 700° C the liquid holding capacity with respect to the test liquid exceeds the arbitrary value of 31%, which is the minimum requirement for a solid state diluent or carrier material for pesticides.

EXAMPLE 4

Absorbency of Attapulgite With Substances Other Than Perlite Added Thereto

Various substances were tested, as additives to attapulgite, to determine whether or not any increase in the absorbency of the attapulgite could be achieved. The substances were chosen on the basis of availability, chemical structure and physical properties, and on the basis of bulk availibility on a commercial scale. The substances tested as additives were:
Vermiculite — exfoliated
Pyrophyllite — bloated
Asbestos fibres
Diatomite
Fly ash
Porous brick grog.

The attapulgite used was representative of that obtainable from the Springbok Flats area, and it was crushed, milled and screened to provide a powder having a grain size of −200, i.e. so that the powder would pass through a screen having openings the size of which was 200 microns. The additives, as listed above, were each milled and screened to fineness of −350, i.e. so that they would pass through a screen having 350 micron openings. The attapulgite was divided into six portions to which were added respectively the above additives, such that in each case the additive formed 20% by weight of the mixture. After addition dry mixing was effected, and each portion was treated with excess water until all the material was in suspension. Flocculation and settling were effected by means of Superfloc, and excess water was decanted. The resulting residue was then dried, crushed, milled and screened to obtain the following particle size fractions:

−850, + 600
−600, + 425
−425, + 300

Equal portions of each fraction were recombined to obtain samples with a particle size distribution of −850, + 300. Each sample was divided into two portions designated A and B.

All the A portions were fired to 500° C and soaked at this temperature for 2 hours; and All the B portions were fired to 750° C and soaked at that temperature for 2 hours.

Absorbency tests were then carried out using the test liquid. The results of the absorbency tests are shown in Table VI hereunder, together with a control test conducted with natural attapulgite granules, and a control test with perlite as additive in which the perlite formed 20% of the mixture.

TABLE VI

Liquid holding capacity for attapulgite with various additives and having a particle size distribution of −850, + 300.

| Firing temperature | 500° C | 750° C |
|---|---|---|
| Additives | 2 hours | 2 hours |
| None-Natural granules - Control | 23.8 | 28.1 |
| 20% Perlite - Control | 37.5 | 42.9 |
| 20% Vermiculite | 23.8 | 24.9 |
| 20% Pyrophyllite | 24.3 | 25.2 |
| 20% Asbestos fibre | 29.2 | 30.2 |
| 20% Diatomite | 31.4 | 33.7 |
| 20% Fly ash | 23.8 | 26.4 |
| 20% Porous brick grog | 23.1 | 24.8 |

CONCLUSIONS

Apart from perlite, only diatomite and asbestos fibre were found significantly to increase the absorbency of the attapulgite. Of these, only the diatomite was found to be able to increase the absorbency of attapulgite above the arbitrary level of 31%, which is acceptable for a solid state diluent for pesticides, but it was found to be unsuitable as a carrier material, as discussed hereunder, owing to the effect on the pH of the product.

EXAMPLE 5

Tests Conducted With Reference to Constructed Granules of Attapulgite, in Which the Granules Were Constructed by a Test Method Which Included Extrusion.

Tests were conducted on the attapulgite with no additions, and with additions of perlite in which perlite made up 20% by weight of the total mixture.

A representative Springbok Flats attapulgite was used in the tests.

Samples of the attapulgite were dried at 120° C to constant weight, crushed, milled and screened to give a powder having a particle size of −200. The powder was divided into two portions designated A and B.

Portion A was mixed with water until plastic and extruded.

Portion B was dry mixed with perlite so that the perlite formed 20% by weight of the mixture. Water was then added until the mixture was plastic, and the mixture was extruded.

In each case the extrusion was such as to produce bars of the extruded material, and was carried out with no vacuum. After extrusion the bars were dried at 120° C to constant weight, followed by crushing, milling and screening to give the following fractions according to particle size:

−850, + 600
−600, + 425
−425, + 300

Each of the fractions obtained for samples A and B was divided into three equal portions which were treated as follows:

One portion of each fraction of each sample was redried at 120° C for 2 hours;

Another portion of each fraction of each sample was fired to 500° C and soaked at that temperature for 2 hours; and The third portion of each fraction of each sample was fired to 750° C and soaked at that temperature for 2 hours.

Absorbency tests were then conducted to establish the liquid holding capacity of the various portions, using both kerosene and the test liquid as absorbates. The results are set out in the following Tables.

TABLE VII

Absorbency test results for attapulgite in the form of constructed particles in which the construction includes extrusion.

| | | Liquid holding capacity | | | |
|---|---|---|---|---|---|
| | | Attapulgite no perlite addition | | Attapulgite 20% perlite addition | |
| Treatment | Particle size fraction | Kerosene | Test liquid | Kerosene | Test liquid |
| Dried at 120° C for 2 hours | −850, + 600 | 15.3 | 19.2 | 21.9 | 25.9 |
| | −600, + 425 | 15.3 | 19.2 | 21.9 | 25.9 |
| | −425, + 300 | 14.5 | 20.0 | 21.9 | 25.9 |
| Fired at 500° C for 2 hours | −850, + 600 | 19.9 | 23.1 | 24.2 | 28.6 |
| | −600, + 425 | 19.9 | 23.1 | 24.2 | 28.6 |
| | −425, + 300 | 19.9 | 23.1 | 24.2 | 28.6 |
| Fired at 750° C for 2 hours | −850, + 600 | 20.6 | 25.9 | 27.5 | 31.1 |
| | −600, + 425 | 20.6 | 25.9 | 27.0 | 31.1 |
| | −425, + 300 | 20.6 | 25.9 | 26.5 | 31.1 |

TABLE VIII

Absorbency test results for constructed particles (extruded) having a particle size distribution of −850, + 300 made up of equal quantities of −850, + 600, −600, + 425 and −425, + 300 fractions.

| | | Liquid holding capacity | | | |
|---|---|---|---|---|---|
| Particle size fraction | Treatment | Attapulgite no perlite added | | Attapulgite 20% perlite added | |
| | | Kerosene | Test liquid | Kerosene | Test liquid |
| −850, | Dried at 120° C 2 hours | 15.0 | 19.5 | 21.9 | 25.9 |

-continued

| Particle size fraction | Treatment | Liquid holding capacity | | | |
|---|---|---|---|---|---|
| | | Attapulgite no perlite added | | Attapulgite 20% perlite added | |
| | | Kerosene | Test liquid | Kerosene | Test liquid |
| + 300 | Fired at 500° C 2 hours | 19.9 | 23.1 | 24.2 | 28.6 |
| | Fired at 750° C 2 hours | 20.6 | 25.9 | 26.9 | 31.1 |

CONCLUSIONS

Extruded granules having no perlite addition showed a decrease in liquid holding capacity when compared with natural granules. Extruded granules with 20% perlite addition showed a decrease in liquid holding capacity when compared with constructed granules with 20% perlite as described in Example 3 above. The process of Example 5 which includes extrusion is thus not as successful as the process of Example 3, with respect to attapulgite, for producing a solid state diluent for pesticides. It nevertheless provides a practical method for increasing the absorbency of the original attapulgite, so that in one case its liquid holding capacity exceeded 31%.

EXAMPLE 6

Heat activation (firing) effects on the absorbency of attapulgite

Tests were conducted to determine the heat activation or firing effects on the absorbency of a representative attapulgite from the Springbok Flats area.

The tests were carried out on natural granules as prepared according to Example 1, constructed granules with no perlite as set out in Example 2 and constructed granules with 20% perlite as set out in Example 3. The particle size fraction of the natural granules used was −850, +600, and that for constructed granules, depending on the test, was −850, +600 or −600, +425. Absorbency tests were conducted to establish the liquid holding capacities using kerosene and the test liquid as absorbates. The test results are set out in the following tables.

TABLE IX

The effects of firing temperature and soaking time on the liquid holding capacity of natural attapulgite granules using kerosene as absorbate.

| Material | Temperature | No soak | 2 hours soak | 4 hours soak |
|---|---|---|---|---|
| Natural granules −850, + 600 | 120° C | 16.9 | 18.3 | 16.3 |
| | 300° C | 17.6 | 18.3 | 18.3 |
| | 500° C | 18.9 | 21.5 | 21.5 |
| | 700° C | 20.8 | 22.0 | 22.6 |
| | 900° C | 23.2 | 12.0 | 12.0 |

TABLE X

The effects of firing temperature and soaking time on the liquid holding capacity of −850, +600 constructed attapulgite granules with no perlite addition and with 20% perlite addition, and with no period of soak.

| Temperature | 300° C | | 500° C | | 700° C | | 900° C | |
|---|---|---|---|---|---|---|---|---|
| | Kerosene | Test liquid | Kerosene | Test liquid | Kerosene | Test liquid | Kerosene | Test liquid |
| Constructed granules no perlite addition −850, + 600 | 16.3 | 21.6 | 20.2 | 26.6 | 20.8 | 27.9 | — | — |
| Constructed granules with 20% perlite | 21.9 | 30.1 | 24.2 | 35.1 | 29.5 | 37.1 | 32.9 | 40.3 |

TABLE XI

Effects of soaking period on natural and constructed attapulgite granules with no perlite addition and with 20% perlite addition at a constant temperature of 500° C and a particle size fraction of −600, +425

| Soaking time in hours | 0 | | 2 | | 4 | |
|---|---|---|---|---|---|---|
| Material | Kerosene | Test liquid | Kerosene | Test liquid | Kerosene | Test liquid |
| Natural granules | 18.6 | 23.8 | 19.6 | 24.5 | 20.8 | 24.5 |
| Constructed granules No perlite addition | 19.6 | 24.5 | 19.6 | 24.5 | 24.6 | 29.8 |
| Constructed granules 20% perlite | 24.7 | 35.5 | 27.2 | 36.5 | 28.0 | 40.3 |

CONCLUSIONS

Temperature effects

Generally the liquid holding capacity increased substantially with increases in temperature, except for the 2 and 4 hour soaks for natural granules at 900° C shown in Table IX, where the liquid holding capacity was less than at lower temperatures.

Soaking effects

In each case an increase in soaking time results in maintenance or an increase in liquid holding capacity, except for the natural granules of attapulgite soaked for 4 hours at 120° C and soaked for 2 hours and 4 hours at 900° C shown in Table IX.

EXAMPLE 7

Tests regarding factors which influence the pH of solutions formed by dispersing in water natural and constructed granules Tests were conducted with attapulgite for natural granules and constructed granules fired at various temperatures, and with perlite and diatomite as additives. The tests were conducted with 90 ml neutral water in which 10 g. of the granules had been stirred for a period of 10 minutes. The tests were conducted with a METROPM pH meter, and were conducted for the purpose of determining the effects on pH of the additives and the firing temperatures and soaking times.

For use in solid state pesticides, the pH obtained according to the above tests should ideally be between about 7 and about 9. A pH between 9 and 10 is still acceptable whereas pH's above 11 are completely unacceptable. At temperatures below about 550° C the pH obtained varied from about 8.1 up to about 9.0; at temperatures between about 550° and about 700° C the pH obtained varied from about 9.0 up to about 10.0; and at temperatures above 800° C the pH rose from about 10.7 at 800° C to about 11.2 at 900° C.

It was found that the pH of solutions in which the granules were stirred increased as the firing temperatures of the granules was increased. It was found that the addition of perlite had no effect on the pH of the constructed granules, when compared with natural granules. On the other hand, it was found that the inclusion of diatomite in constructed granules led to substantial increases in pH.

Certain toxicants in solid state pesticides are incompatible with carrier materials which are basic in the sense that when stirred in water they lead to a solution which has an excessively high pH, the basicity of the carrier material leading to deterioration of the toxicant. From the tests it is thus apparent that diatomite is unsuitable for toxicants which are intolerent of basicity in the carrier material. Furthermore for such toxicants careful control of the firing temperature may be required, for attapulgite to which perlite is added to keep the firing temperature below those at which the carrier material is excessively basic.

EXAMPLE 8

Detailed investigation into the efficient heat activation of attapulgite

The following tests were conducted to determine the effects on the liquid holding capacity of attapulgite of variations in activation temperature and soaking period. Three types of attapulgite granules were used in the tests, namely natural granules the preparation of which is set out in Example 1 (Type N); constructed granules with 10% perlite, the preparation of which is set out in Example 3 (designated type C/10); and constructed granules with 20% perlite and the construction of which is set out in Example 3 (designated type C/20). The particle size fraction used in the tests was −600, + 425. All granules were dried at 120° C for 2 hours before testing commenced.

Soaking period test

These tests were conducted at 500° C and 750° C, the temperature being held constant in each case while the soaking periods were increased. Examples of each type of granules were placed in an electric furnace which had previously been brought to the selected temperature, and samples were withdrawn at the following intervals:

| ½ hour  | 1 hour  | 1½ hour  | 2 hours | 3 hours |
| 4 hours | 6 hours | 10 hours |         |         |

After soaking absorbency tests were conducted to establish the liquid holding capacities of the samples with respect to kerosene and the test liquid as absorbates.

Activation temperature test

From the soaking period tests a soaking period of 2 hours was selected as being a suitable soaking period. In the activation (firing) temperature test 21 samples of each type of granule were prepared. The temperature selected for testing were between 500° C and 900° C, there being a 20° increment between each succeeding temperature. A sample of each granule type was tested at each temperature. Temperature fluctuations were held to a minimum during loading and unloading, and temperature was held constant throughout the 2 hour soaking period. After soaking absorbency tests were conducted.

Soaking period tests are set out in the following Tables:

TABLE XII

Liquid holding capacities for −600, +425 particle size fractions fired at 500° C

| Soaking time in hours | Liquid holding capacity | | | | | |
|---|---|---|---|---|---|---|
| | Type N | | Type C/10 | | Type C/20 | |
| | Kerosene | Test liquid | Kerosene | Test liquid | Kerosene | Test liquid |
| ½  | 21.3 | 25.2 | 23.7 | 28.6 | 27.3 | 32.8 |
| 1  | 21.3 | 24.5 | 25.4 | 31.6 | 29.6 | 36.0 |
| 1½ | 21.3 | 25.2 | 26.5 | 32.8 | 31.5 | 37.0 |
| 2  | 21.3 | 25.2 | 27.3 | 32.8 | 33.8 | 38.5 |
| 3  | 21.3 | 25.2 | 28.1 | 33.3 | 33.3 | 38.5 |
| 4  | 21.3 | 25.2 | 28.6 | 33.9 | 33.3 | 38.5 |
| 6  | 21.3 | 25.2 | 28.6 | 33.9 | 33.3 | 38.5 |
| 10 | 21.3 | 25.2 | 28.6 | 33.9 | 33.3 | 38.5 |
| Cf. | | | | | | |
| Dried at 120° C | 17.6 | 21.4 | 24.9 | 32.8 | 29.5 | 36.5 |

TABLE XII

Liquid holding capacities for −600, + 425 particle size fractions fired at 750° C

| Soaking time in hours | Liquid holding capacity | | | | | |
|---|---|---|---|---|---|---|
| | Type N | | Type C/10 | | Type C/20 | |
| | Kerosene | Test liquid | Kerosene | Test liquid | Kerosene | Test liquid |
| ½  | 21.3 | 25.2 | 26.5 | 31.6 | 29.6 | 35.5 |
| 1  | 21.9 | 26.6 | 27.0 | 32.8 | 30.5 | 36.5 |
| 1½ | 22.5 | 26.6 | 27.3 | 33.3 | 32.4 | 38.5 |
| 2  | 22.5 | 26.6 | 27.3 | 33.3 | 34.2 | 39.9 |
| 3  | 22.5 | 26.6 | 28.6 | 33.9 | 35.9 | 41.2 |
| 4  | 22.5 | 26.6 | 28.6 | 33.9 | 35.9 | 41.2 |
| 6  | 22.5 | 26.6 | 28.6 | 33.9 | 35.9 | 41.2 |
| 10 | 22.5 | 26.6 | 28.6 | 33.9 | 35.9 | 41.2 |

Activation temperature test results are set out in the following Tables:

TABLE XIV

Liquid holding capacities for −600, + 425 particle size fractions fired at various temperatures with a soaking period of 2 hours at each temperature. The test liquid was used to determine the liquid holding capacity.

| Activation temperature °C | Liquid holding capacity | | |
|---|---|---|---|
| | Type N | Type C/10 | Type C/20 |
| 500 | 25.2 | 29.8 | 33.3 |
| 520 | 26.6 | 30.4 | 33.9 |
| 540 | 26.6 | 31.0 | 33.9 |
| 560 | 26.6 | 33.3 | 34.4 |
| 580 | 25.2 | 33.3 | 36.0 |
| 600 | 25.2 | 31.0 | 35.5 |
| 620 | 26.6 | 35.5 | 38.5 |
| 640 | 26.6 | 36.5 | 39.4 |
| 660 | 26.6 | 36.5 | 40.3 |
| 680 | 26.6 | 37.0 | 40.7 |
| 700 | 26.6 | 37.0 | 42.0 |
| 720 | 26.6 | 37.0 | 39.9 |
| 740 | 27.9 | 37.0 | 41.2 |
| 760 | 26.6 | 36.5 | 41.6 |
| 780 | 25.2 | 35.5 | 41.2 |
| 800 | 23.1 | 31.6 | 37.0 |
| 820 | 20.0 | 29.2 | 33.9 |
| 840 | 13.0 | 27.3 | 32.8 |
| 860 | 12.1 | 25.9 | 32.8 |
| 880 | 11.1 | 25.9 | 32.8 |
| 900 | 11.1 | 25.9 | 32.8 |

CONCLUSIONS

From Tables XII and XIII it appeared that in each case, except for the Type N granules in Table XII, an increase in liquid holding capacity resulted from an increased in soaking time. At an activation or firing temperature of 500° C improvements in liquid holding capacity appeared to be confirmed to the first 2 hours of soak, further soaking leading to no further increase. At an activation temperature of 750° C, all the improvements in liquid holding capacities took place in the first 3 hours of soaking, there being no further increases for soaking periods exceeding three hours.

From Table XIV it is apparent that for each granule type improvement of liquid holding capacity took place when the temperature was increased above 500° C, up to a maximum, after which liquid holding capacity decreased as 900° C was approached. For Type N granules (natural) the optimum temperature appeared to be 740° C; for type C/10 granules (10% perlite) the optimum temperature appeared to be 680° C; and for type C/20 granules (20% perlite) the optimum temperature appeared to be 700° C.

EXAMPLE 9

The following tests were carried out on constructed granules, constructed according to the procedure set out in Example III. Samples were constructed from attapulgite, having various proportions of perlite added thereto. The additions of perlite in terms of weight percent of the mixture, are set out as follows, together with the designation of the samples:

| % Perlite addition | Sample Designation |
|---|---|
| 1 | C/1 |
| 2 | C/2 |
| 3 | C/3 |
| 4 | C/4 |
| 5 | C/5 |
| 6 | C/6 |
| 7 | C/7 |
| 8 | C/8 |
| 9 | C/9 |
| 10 | C/10 |
| 12 | C/12 |
| 14 | C/14 |
| 16 | C/16 |
| 18 | C/18 |
| 20 | C/20 |
| 30 | C/30 |

The particle size fractions used for the tests in this example were as follows:
- −850, +600 fractions were loaded into a cold electric furnace and were fired to 750° C. When 750° C was reached, the samples were immediately removed. Firing temperature and soaking time are designated 750/0;
- −600, +425 particle size fractions were loaded into an electric furnace which had been previously brought to a temperaure of 500° C and were soaked for a period of 2 hours. These samples are designated 500/2;
- −425, +300 particle size fractions were loaded into an electric furnace which had previously been brought to a temperature of 450° C, and were soaked for 4 hours. These samples are designated 450/4.

Liquid holding capacity tests were carried out on the various samples, using the test liquid as absorbate. The test results are set out in the following Tables.

TABLE XV

| Designations | Liquid holding capacity | | |
|---|---|---|---|
| | 750/0 | 500/2 | 450/4 |
| C/1 | 26,3 | 25,4 | 25,9 |
| C/2 | 26,3 | 25,4 | 25,9 |
| C/3 | 29,9 | 27,5 | 26,5 |
| C/4 | 31,9 | 27,5 | 27,5 |
| C/5 | 32,3 | 28,1 | 27,5 |
| C/6 | 35,8 | 29,1 | 27,5 |
| C/7 | 36,5 | 29,1 | 28,1 |
| C/8 | 37,1 | 30,1 | 28,1 |
| C/9 | 36,5 | 31,0 | 28,1 |
| C/10 | 37,1 | 32,4 | 29,1 |
| C/12 | 37,7 | 32,4 | 29,1 |
| C/14 | 38,6 | 33,3 | 29,1 |
| C/16 | 39,4 | 35,5 | 30,6 |
| C/18 | 39,9 | 38,3 | 31,0 |
| C/20 | 42,1 | 38,3 | 31,5 |
| C/30 | 43,1 | 39,4 | 31,5 |

CONCLUSIONS

It is clear from the test results that stepwise increases in the proportion of perlite lead to stepwise increases of the liquid holding capacity of the product. The effect is relatively rapid until perlite amounts to 10% of the mixture, after which the rate of improvement is slower until 30% perlite is reached. Above 30% perlite, the particles became too soft to test reliably.

Discussion of Test Results

From the aforegoing examples it is clear that the process of the invention provides a practical and commercially attractive method for producing a carrier material for pesticides from low grade attapulgite. The invention thus provides a process whereby large deposits of attapulgite, which are of low absorbency and are unsuitable when fired for use as solid state diluents in pesticides, can be altered by increasing their absorbency to produce a product suitable for use as a carrier material in a pesticide. The tests show that in every case attapulgite treated according to the process of the invention with perlite had its absorbency increased. Tests based on attapulgite and using diatomite and asbestos fibre as additives, also showed increases in absorbency, but the low increases, and in the case of diatomite, the effect on pH, ruled them out as effective additives.

A popular particle size fraction for solid state diluents is −600, +300 with respect to micron screen sizes, and for this particle size fraction in the finished product, the process displays some of its best results.

The best additive was found to be perlite, which is relatively chemically inert. The addition of perlite to attapulgite thus has no adverse effect as regards chemical properties of the product, when compared with the fired clay with no additives, relative to toxicants. In other words, any adverse chemical properties such as an excessively high pH, in carrier materials produced according to the process, are believed to stem from properties of the starting attapulgite, and not from the addition of perlite. These adverse characteristics can thus be avoided by controlling firing temperatures to below specific limits.

In this specification, as mentioned above, all particle size fractions and screen sizes or the like given numerically relate to screen opening sizes in microns, except where otherwise specified as ASTM-screen sizes. In this regard it should be noted that the perlite used in each case is extremely difficult to screen, and is in fact separated in practice by other methods of classification into particle size fractions. The perlite used however has a particle size, determined microscopically, in the region of about 30 – 60 microns, thus corresponding with a 300 mesh ASTM screen opening. Suitable perlite is available from Perlite Industries (Proprietary) Limited, P.O. Olifantsfontein, Transvaal Province, Republic of South Africa under the trade designation Grade 60/90.

The invention lends itself easily to adaptation for large scale commercial or industrial production. Attapulgite as mined in the Springbok Flats area is readily crushed, ground, milled and screened into a fine powder suitable for use as a starting material, the attapulgite being relatively friable when dry. The attapulgite is inexpensive, and suitable perlite is available in sufficient quantities and at a prices suitable to render the process commercially attractive. It is contemplated that dry mixes will be made of the attapulgite powder and perlite in desired proportions, which will be, either continuously or batchwise, brought into suspension in tanks of water, which water is preferably neutral with respect to pH, or has a suitable pH to compensate for excessive alkalinity or acidity in the starting material. The aqueous suspension of the starting materials will be caused to settle, preferably by means of Superfloc or a similar organic flocculant, to produce a residue or sludge which will then be dried into a cake which will then be crushed, ground, and then milled and screened to have the desired particle size distribution for the final product. The crushed cake will then be fired, again either batchwise or continuously, in a kiln, oven, furnace or the like, to a suitable firing temperature and for a suitable soaking period. The product will then be ready for storage, transport or use, as soon as it has been fired.

When the cake is crushed prior to firing, oversize particles from the crushed cake can readily be recycled through the grinding and milling steps; and undersize fines can readily be recycled through the mixing step as the dried cake is still in the form of a clay and will readily go into suspension. It is possible, instead, to fire the cake before crushing thereof, and crush, grind and mill and screen the fired product. This procedure yields the same granular product, and as in the case of crushing before firing, the fines may be returned to the mixing step, the oversize being returned to the grinding and milling steps.

As regards the initial mixing step, the relative amounts of water and solids will depend on practical consideration, bearing in mind that sufficient water will be necessary to get the clay into suspension in a sufficiently finely divided form, to form an intimate mixture with the perlite or other additives. In this regard it is contemplated that the water used will be set at a minimum consistant with a suitable product to facilitate settling. Furthermore, use can be made of mechanical agitation and stiring, of a type which causes some comminution of the feed materials. Thus feed materials may be introduced into the mixing step in a somewhat coarser form than would otherwise be the case, the feed materials being wet-milled during the mixing step. This can be effected by blunging the feed materials in a blunger.

The applicant has also found that when phosphoric acid is added during the initial mixing step in quantities between 0.2 and 0.5% by weight of the total solids, a final granular product is obtained which is more resistant to attrition than the product obtained without the phosphoric acid. It is thus contemplated that, where necessary, phosphoric acid will be used in the process, in these quantities, when minimum water is used in the mixing step. Clearly, when mixing is performed with excess water, more phosphoric acid will have to be added, to achieve the same degree of strengthening of the final product.

From the aforegoing examples, it is apparent that the chief parameters whereby increase in absorbency may be varied, for a fixed starting product, are the firing temperature, soaking period and the proportion of additive. To produce a product having a particular specification with respect to absorbency, from a starting material having a particular absorbency, both the firing temperature, the soaking period and the proportion of perlite added can be varied as desired. Thus, for example, for higher firing temperatures a lower proportion of perlite will be required, to achieve a particular absorbency in the product, than will be the case with lower firing temperatures. Thus, depending on the economics, it will be relatively simple to determine experimentally the optimum values for firing temperature, soaking period, and proportion of additive, in a particular situation. Thus in areas where perlite is expensive and power is inexpensive, higher firing temeratures and lower proportions of perlite may be used than in areas where perlite is less expensive and power is more expensive. The facility for varying the firing temperature, the soaking period and the proportion of additive thus adds great flexibility in practice to the process.

It should be noted that, when producing a carrier material having an absorbency of 31% or more, it is possible to produce a robust product having a resistance to attrition which is comparable with that of high grade attapulgite which has previously been used, as a carrier material. Fines production in manufacture, transport, storage and use is not excessive, and is at acceptable levels. In this regard it is further to be noted that resistance to attrition decreases with increased proportions of perlite relative to clay in the feed material. The strength of the product when the perlite is above 20% by weight of the mixture renders it unsuitable for use as a carrier material, and it is necessary for this reason to keep the proportion of perlite below about 20%. Variations in firing temperature, soaking period and proportions of starting materials should thus be controlled, not only to achieve a desired absorbency in the product, but also to achieve a desired resistance to attrition in the product. As mentioned above, however, these variations will depend on economic considerations and also on the quality and properties of the starting attapulgite.

Also, the invention has the advantage that, although a versatile carrier material can be produced with perlite from attapulgite, having an absorbency of 31% and hence suitable for use with most toxicants in solid state pesticides, it will in practice not always be necessary to have such a high absorbency. Thus, for a particular application with a particular toxicant, the process can be tailored, by reducing the firing temperature and by reducing the proportion of perlite added, to achieve an increase in absorbency which is no more than is necessary. This leads to resultant economy in production. The bulk density of carrier materials produced according to the process of the materials is at a suitable value for solid diluents, and is roughly a third lower than that for natural high grade attapulgite, after firing.

It is regarded as essential to the invention that the firing be to a temperature between 450° and 780° C; that less than 20% perlite be used in the mixture; and that the particle size of the attapulgite and perlite in the mixture which forms the cake be smaller than 150 ASTM mesh.

These aspect are discussed in some detail, as follows.

FIRING TEMPERATURE

Maximum

From Table XIV it is clear that any increase above 780° C in firing temperature is counter productive and leads to a decrease in absorbency. For this reason, in practice, a firing temperature of above 780° C would never be considered, for any reason whatsoever. Furthermore as no substantial increase in absorbency takes place above 700° C, it is felt that, for reasons of economy, firing temperatures above 700° C will rarely be used. In fact, in practice as shown for C/10 and C/20 in Table XIV and for 500/2 in Table XV, it is anticipated that the bulk of commercial production will involve firing temperatures of below 600° C.

Another aspect which limits the firing temperature to 780° C is apparent from Example 7. At a firing temperature of 800° C the pH of the product (10.7) is so high that there are a number of toxicants for which it would be unsuitable. Thus a firing temperature of above 780° C would very rarely, if ever, be practicable. At firing temperatures between 550° and 700° C the pH is unacceptable for only a few toxicants and to operate in this temperature range would be a commercial proposition. Below 550° C the product would be substantially suitable as a universal carrier material for pesticides, as regards pH.

Without wishing to be bound by theory, the applicant believes that phase changes commence in the attapulgite (irreversible) at about 780° – 800° C in which it is converted to different substances of lower absorptivity e.g. corderite and crystobalite. Also the higher the firing temperature, the greater are the proportions of magnesium and calcium carbonates which are converted into basic oxides, leading to high pH.

Minimum

450° C is set as the minimum firing temperature as it is believed by the applicant that firing to this temperature initiates the driving off of crystals or lattice water in the attapulgite. Firing to this temperature ensures that the attapulgite is irreversibly changed from its phase in which it forms a plastic solid or suspension with water, to its phase in which it does not form such plastic solid or suspension. This is important as a good carrier material should not, in the field when exposed to rain, snow etc. easily degrade into a sludge or suspension which can be washed away and lost.

PROPORTIONS OF PERLITE

Maximum

The maximum proportion of perlite is set at 20% by weight because (e.g. Table XV) increase above this limit results in a marginal increase in absorbency. At the same time the applicant has found that a substantial reduction in resistance to attrition takes place. In practice use of a carrier material with above 20% perlite would lead to excessive fines of dust production, leading to loss of free flowing characteristics in extreme cases, waste through wind loss in the field, and difficulty in handling. Such product (i.e. above 20% perlite) would thus not find commercial application as a carrier material. Furthermore, as perlite is the more expensive constituent, the increase in cost from using more than 20% perlite would not be justified by the small increase in absorbency, bearing in mind the fines disadvantage.

Minimum

The minimum perlite addition is set at 3% as this level is the minimum required for a measureable increase in absorbency (Table XV). Although this does not increase absorbency of the attapulgite tested with the test liquid to above 31%, it will be appreciated that operation at this level may be an advantage and sufficient when a lower grade of final product (with respect to absorbency) is required, or a higher grade starting attapulgite is available.

In practice however it is contemplated that most commercial production will take place in the range between 8 and 15% perlite by weight.

PARTICLE SIZE

A maximum particle size for the constituents in the mixture of 150 ASTM mesh is required for several reasons. The practical reason is that the applicant believes that, in the mixture bonding between the attapulgite particles is by electrostatic bonding and van der Waal's forces (once again without wishing to be bound by theory). The perlite is believed to be inert in this regard and thus the smaller the perlite particles, the better they will be trapped and enclosed in a matrix of attapulgite, and there are less likely to be zones of excessive weakness at the perlite particles. The mechanism of bonding in this regard is to be contrasted with strong ceramic bonding which takes place in the clay matrix in clays treated to above 800° C or more, and which would render particle size considerations in the perlite which could lead to weakness, irrelevant. In this regard it is to be noted that it is preferred to use on the one hand very fine perlite and on the other hand attapulgite which is sufficiently fine to go into suspension easily and rapidly during the mixing step, in the form of particles of almost colloidal size which agglomerate to form the cake on settling and drying.

A further important aspect regarding the perlite particle size is that, by operating at −150 ASTM mesh, and preferably between 300 and 400 ASTM mesh, the perlite used may be entirely waste material which is generally too fine to be used commercially. In this regard it is to be noted that the finest filter grade perlite, which to the applicant's knowledge, is sold in bulk quantities on an industrial or commercial scale is of a perlite size between 100 ASTM mesh and 150 ASTM mesh.

I claim:

1. A process for producing a granular carrier material for pesticides from attapulgite which includes the steps of:
   a. wet mixing perlite and attapulgite together in an aqueous medium to form a cake which comprises an intimate mixture of between 97 and 80% by weight of attapulgite in finely divided form and between 3 and 20% by weight of heat expanded perlite in finely divided form, the attapulgite and perlite being of a particle size capable of passing through a 150 mesh ASTM screen;
   b. heating the cake to a temperature of between 450° and 780° C; and
   c. breaking up the cake to form a granular solid.

2. A process as claimed in claim 1, in which the mixture comprises between 92 and 85% by weight attapulgite, and between 8 and 15% by weight perlite.

3. A process as claimed in claim 1, in which the cake is heated to a temperature of between 500° and 700° C.

4. A process as claimed in claim 3, in which the cake is heated to a temperature between 500° and 600° C.

5. A process as claimed in claim 1, which includes the step of, after heating the mixture, maintaining the mixture at the temperature to which it is heated for a soaking period of up to 3 hours.

6. A process as claimed in claim 5, in which the soaking period is between 1 and 2 hours.

7. A process as claimed in claim 1, in which the wet mixing comprises dispersing the components in the aqueous medium, the mixture being separated from the aqueous medium prior to heating.

8. A process as claimed in claim 7, in which separating the mixture from the aqueous medium is by causing it to settle from the aqueous medium.

9. A process as claimed in claim 8, in which the settling includes flocculating the components by means of an organic flocculant.

10. A process as claimed in claim 1 in which the wet mixing includes adding phosphoric acid to the mixture so that the phosphoric acid forms 0.2 to 0.5% by weight of the total weight of the mixture on a dry basis.

11. A process as claimed in claim 1, whereas the components of the wet mixture are comminuted during said wet mixing step.

12. A process as claimed in claim 1, in which the particle size of the components in the cake is such that the greater proportion by weight of the particles will pass through a 200 ASTM mesh screen but will be retained by a 600 ASTM mesh screen.

13. A process as claimed in claim 12, in which the particle size is such that the greater proportion by weight of the particles will pass through a 300 ASTM mesh screen but will be retained by a 400 ASTM mesh screen.

14. A process as claimed in claim 1, in which the breaking step comprises grinding, the process including the step, after grinding the cake, of classifying the particles formed according to size so that at least 80% by weight of the carrier material will pass through a 20 mesh ASTM screen but will be retained by a 60 mesh ASTM screen.

15. A process as claimed in claim 14, in which the classifying is by screening and is such to classify the particles into three predetermined fractions according to screen opening size in microns, namely one fraction of particle size −850 + 600, another of particle size −600 + 425 and a third of particle size −425 + 300, the screening being followed by the step of recombining the fractions in equal proportions.

16. A process as claimed in claim 14, in which all the particles incapable of passing through a 20 mesh ASTM screen are recycled through the grinding step for additional grinding.

17. A process as claimed in claim 14, in which all the particles capable of passing through a 60 mesh ASTM screen are recycled through the mixing step to form part of the cake.

18. A process as claimed in claim 1, in which the mixture comprises less than 90% attapulgite and more than 10% perlite, and the heating of the cake is to a temperature above 540° C.

19. A grannular carrier material for pesticides, which comprises an intimate mixture of between 97 and 80% by weight of attapulgite and between 3 and 20% by weight of heat-expanded perlite, the perlite being in the form of particles having a particle size capable of passing through a 150 mesh ASTM screen, and being randomly dispersed throughout a matrix of attapulgite particles which is formed by heating a wet mix of the perlite and attapulgite particles capable of passing through a 150 mesh ASTM screen to a temperature of between 450° and 780° C.

20. A carier material as claimed in claim 19, which comprises less tha 90% attapulgite and more than 10% perlite, the matrix being formed by heating to a temperature of above 540° C.

21. A carrier material as claimed in claim 20, which is capable of absorbing a liquid comprising 77% by weight of benzyl chloride (alpha chlorotoluene) and 23% by weight of petroleum benzine, to form a free-flowing grannular product comprising at least 30% by weight of the liquid.

22. A carrier material as claimed in claim 19, which comprises between 92 and 85% by weight of attapulgite, and between 8 and 15% by weight of perlite.

23. A carrier material as claimed in claim 19, in which the matrix is formed by heating to a temperature between 500° and 700° C.

24. A carrier material as claimed in claim 19, in which the matrix is formed by heating to a temperature between 500° and 600° C.

25. A carrier material as claimed in claim 19, in which the matrix is formed by soaking the wet mix at the temperaure to which it is heated for a period of up to 3 hours.

26. A carrier material as claimed in claim 19, which comprises between 0.2 and 0.5% by weight of phosphoric acid.

27. A carrier material as claimed in claim 19, which has a particle size distribution such that it comprises three fractions of equal weight, namely one fraction of particle size −850 + 600, another of particle size −600 + 425, and a third of particle size −425 + 300.

* * * * *